United States Patent
Garrish

(10) Patent No.: US 9,844,454 B2
(45) Date of Patent: *Dec. 19, 2017

(54) BRACE AND TENSION SPRINGS FOR A BRACE

(71) Applicant: Spring Loaded Technology Incorporated, Halifax (CA)

(72) Inventor: Robert Garrish, Halifax (CA)

(73) Assignee: Spring Loaded Technology Incorporated, Halifax, CA (US)

(*) Notice: Subject to any disclaimer, the term of this patent is extended or adjusted under 35 U.S.C. 154(b) by 388 days.

This patent is subject to a terminal disclaimer.

(21) Appl. No.: 14/526,826

(22) Filed: Oct. 29, 2014

(65) Prior Publication Data
US 2015/0119777 A1    Apr. 30, 2015

Related U.S. Application Data

(63) Continuation-in-part of application No. 14/317,447, filed on Jun. 27, 2014, now Pat. No. 9,416,838.

(30) Foreign Application Priority Data
Oct. 31, 2013   (CA) ..................... 2831507

(51) Int. Cl.
*A61F 5/01* (2006.01)

(52) U.S. Cl.
CPC ............ *A61F 5/0123* (2013.01); *A61F 5/013* (2013.01); *A61F 5/0125* (2013.01);
(Continued)

(58) Field of Classification Search
CPC .. A61F 5/00; A61F 5/01; A61F 5/0102; A61F 5/0123; A61F 5/0125; A61F 5/013;
(Continued)

(56) References Cited

U.S. PATENT DOCUMENTS

| | | | |
|---|---|---|---|
| 4,433,679 A | 2/1984 | Mauldin et al. |
| 4,558,767 A | 12/1985 | Taylor |

(Continued)

*Primary Examiner* — Keri J Nelson
(74) *Attorney, Agent, or Firm* — Walker & Jocke

(57) ABSTRACT

A brace for augmenting extension of a user's limb about a joint comprises an upper arm pivotably attached to a lower arm. At least one compression element is attached to at least one of the upper and lower arms, and a substantially inelastic tensioning element is affixed to the other of the upper and lower arms over at least one tensioning member. Applying a force to bend the brace to a flexed position loads the compression element, and upon removal of the flexing force the compression element applies a restoring force to urge the brace back to the extended position. The compression element may comprise a hydraulic tension spring comprising at least one cylinder having a sealed portion defining a liquid containment space, and a piston comprising a compressing portion having a smaller diameter than the cylinder and extending axially through a hydraulic seal into the liquid containment space. A guide for maintaining the piston oriented axially relative to the frame maintains piston alignment so that when the frame is fixed in place and tension is applied to the tensioning member, the compressing portion of the piston rod intrudes further into the liquid containment space, compressing the hydraulic fluid and loading the spring.

20 Claims, 13 Drawing Sheets

(52) U.S. Cl.
CPC ............... *A61F 2005/0134* (2013.01); *A61F 2005/0169* (2013.01); *A61F 2005/0179* (2013.01); *A61F 2005/0197* (2013.01)

(58) Field of Classification Search
CPC ...... A61F 2005/0134; A61F 2005/0137; A61F 2005/0165; A61F 2005/0169; A61F 2005/0179; A61F 2005/0197
USPC ..................................... 602/16, 20, 23, 26
See application file for complete search history.

(56) References Cited

U.S. PATENT DOCUMENTS

| | | | |
|---|---|---|---|
| 4,643,176 A | 2/1987 | Mason et al. | |
| 4,665,905 A | 5/1987 | Brown | |
| 4,751,920 A | 6/1988 | Mauldin et al. | |
| 4,821,707 A | 4/1989 | Audette | |
| 4,846,842 A | 7/1989 | Connolly et al. | |
| 4,928,676 A | 5/1990 | Pansiera | |
| 4,938,207 A | 7/1990 | Vargo | |
| 4,961,416 A | 10/1990 | Moore et al. | |
| 5,042,464 A | 8/1991 | Skwor et al. | |
| 5,107,824 A | 4/1992 | Rogers et al. | |
| 5,261,871 A | 11/1993 | Greenfield | |
| 5,376,137 A | 12/1994 | Shorter et al. | |
| 5,395,304 A | 3/1995 | Tarr et al. | |
| 5,399,149 A | 3/1995 | Frankowiak et al. | |
| 5,437,619 A | 8/1995 | Malewicz et al. | |
| 5,472,410 A | 12/1995 | Hamersly | |
| 5,873,847 A | 2/1999 | Bennett et al. | |
| 6,001,075 A | 12/1999 | Clemens et al. | |
| 6,245,034 B1 | 6/2001 | Bennett et al. | |
| 6,471,664 B1 | 10/2002 | Campbell et al. | |
| 6,500,138 B1 | 12/2002 | Irby et al. | |
| 6,527,733 B1 | 3/2003 | Ceriani et al. | |
| 6,878,126 B2 | 4/2005 | Nelson et al. | |
| 6,890,314 B2 | 5/2005 | Seligman | |
| 7,232,972 B1 | 6/2007 | Yang | |
| 7,507,215 B2* | 3/2009 | Ryan | A61F 5/0123 602/16 |
| 7,553,289 B2 | 6/2009 | Cadichon | |
| 7,608,051 B1 | 10/2009 | Nace | |
| 7,927,299 B2 | 4/2011 | Krause | |
| 7,963,933 B2 | 6/2011 | Nace | |
| 8,057,414 B2 | 11/2011 | Nace | |
| 8,308,669 B2 | 11/2012 | Nace | |
| 8,308,671 B2 | 11/2012 | Nace | |
| 8,328,745 B2 | 12/2012 | Einarsson et al. | |
| 8,376,974 B2 | 2/2013 | Nace | |
| 8,388,564 B2 | 3/2013 | Nace | |
| 8,435,197 B2* | 5/2013 | Vollbrecht | A61F 5/0125 602/23 |
| 8,696,604 B2 | 4/2014 | Kawakami et al. | |
| 8,821,426 B2 | 9/2014 | Einarsson et al. | |
| 8,920,350 B2 | 12/2014 | Merkley et al. | |
| 8,939,924 B1 | 1/2015 | Paulos | |
| 9,022,965 B2 | 5/2015 | Auberger et al. | |
| 9,062,732 B2 | 6/2015 | Aramizu et al. | |
| 9,089,403 B2 | 7/2015 | Nace | |
| 9,113,998 B2 | 8/2015 | Romo | |
| 9,125,730 B2 | 9/2015 | Thor et al. | |
| 9,265,646 B2 | 2/2016 | Nace et al. | |
| 9,333,107 B2 | 5/2016 | Potter et al. | |
| 9,351,864 B2 | 5/2016 | Romo et al. | |
| 9,364,365 B2 | 6/2016 | Omarsson et al. | |
| 9,398,971 B2 | 7/2016 | Chiang et al. | |
| 2007/0010772 A1 | 1/2007 | Ryan | |
| 2013/0110020 A1* | 5/2013 | Ingimundarson | A61F 5/0123 602/16 |
| 2014/0336554 A1 | 11/2014 | Romo et al. | |
| 2015/0005685 A1 | 1/2015 | Chetlapalli et al. | |
| 2015/0005686 A1 | 1/2015 | Kazerounian et al. | |
| 2015/0223958 A1 | 8/2015 | Dunn | |
| 2015/0272811 A1 | 10/2015 | Choi et al. | |
| 2015/0290010 A1 | 10/2015 | Nace | |
| 2015/0374530 A1 | 12/2015 | Bosshard et al. | |
| 2016/0038327 A1 | 2/2016 | Mason et al. | |
| 2016/0058596 A1 | 3/2016 | Chiang et al. | |
| 2016/0120683 A1 | 5/2016 | Romo et al. | |
| 2016/0143763 A1 | 5/2016 | Hsu et al. | |
| 2016/0151189 A1 | 6/2016 | Romo et al. | |
| 2016/0175134 A1 | 6/2016 | Shamaei et al. | |
| 2016/0175135 A1 | 6/2016 | Kahles et al. | |
| 2016/0256310 A1 | 9/2016 | Blecher | |

* cited by examiner

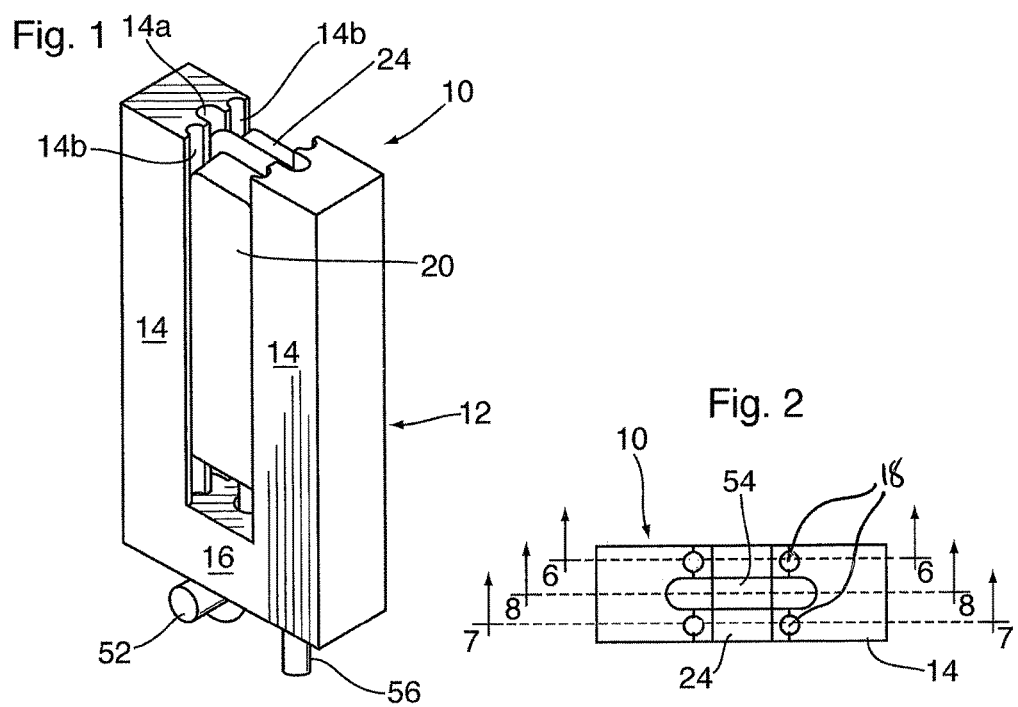
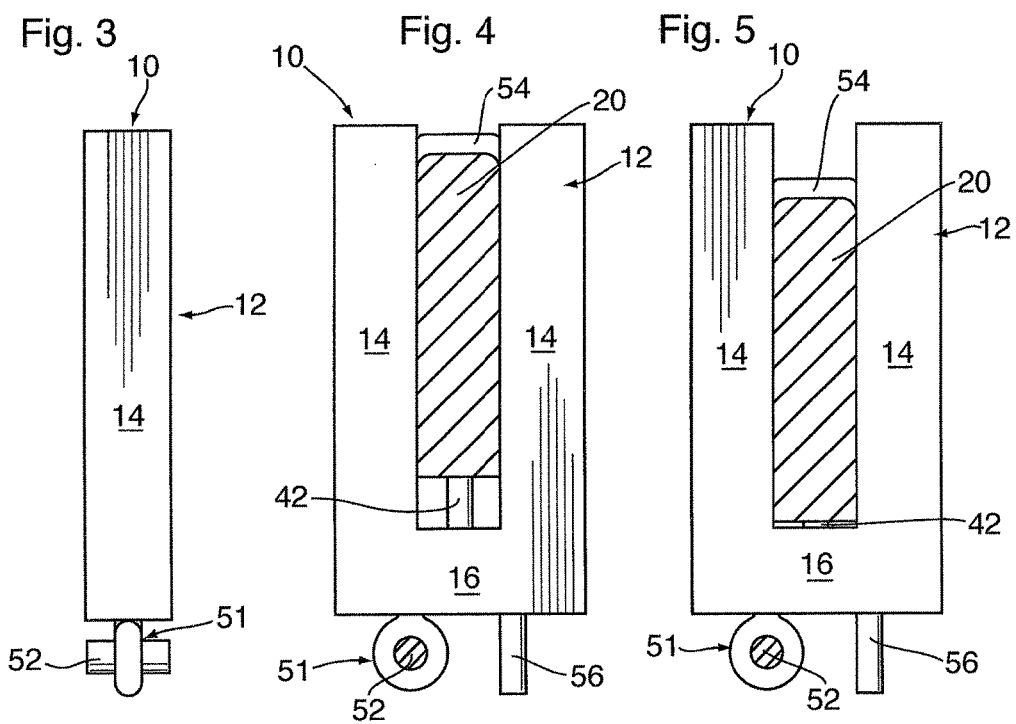

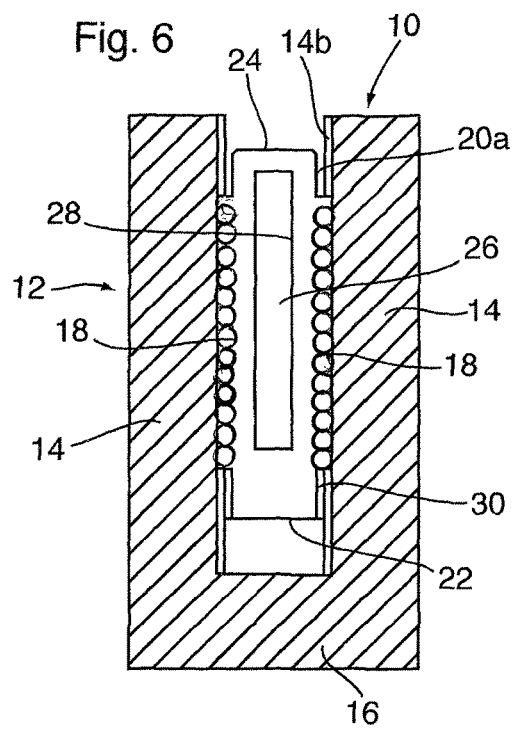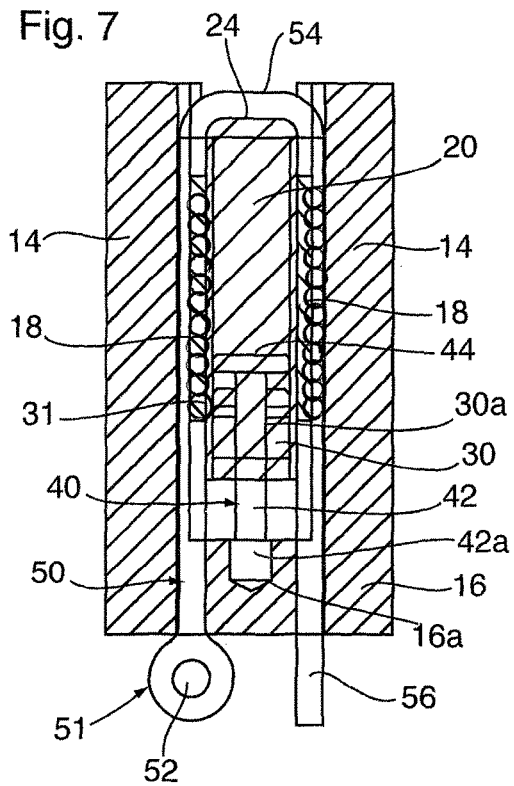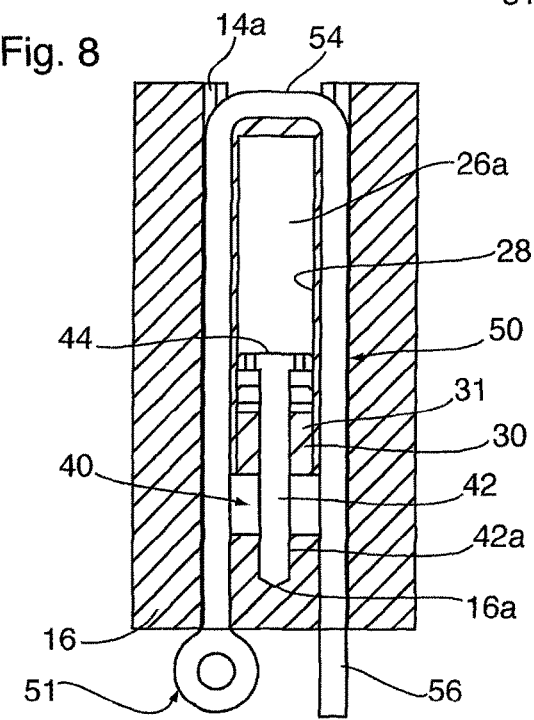

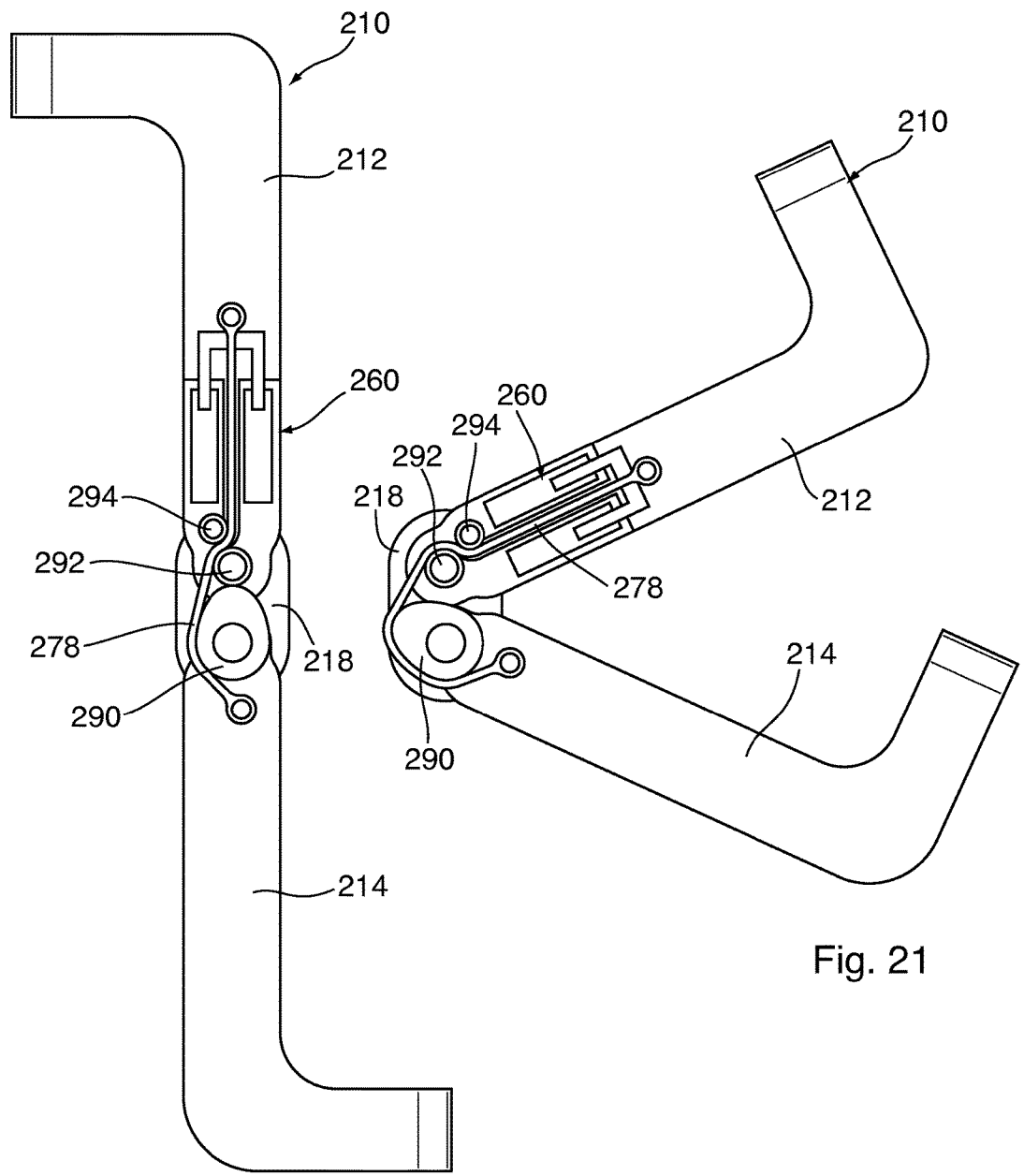

BRACE AND TENSION SPRINGS FOR A BRACE

CONTINUATION DATA

This Application is a continuation-in-part of U.S. application Ser. No. 14/317,447 filed Jun. 27, 2014, which is incorporated by reference herein in its entirety. This Application also claims benefit of Canadian Application No. 2,831,507 filed Oct. 31, 2013.

FIELD OF INVENTION

This invention relates to braces, and in particular a brace for supporting and/or assisting the extension of a limb, and springs used with such braces.

BACKGROUND OF THE INVENTION

As is well known, a knee brace can perform a purely prophylactic function, or provide an assistive force that helps the user to extend their knee, or both. Knee braces can provide physical protection against injury, and may for example be used by athletes involved in high-risk sports where there is a relatively high susceptibility to sustaining a knee injury.

Many individuals suffer from knee problems, often due to a prior knee injury. Some such problems can significantly affect mobility and/or the ability to support the injured person. While corrective measures such as exercise and physiotherapy, or in more serious cases surgery, can assist in correcting or partially alleviating some knee problems, there remains a need in many cases for knee support and extension augmentation.

Particularly where there has been ligament damage, for example a tear or strain in the anterior cruciate ligament (ACL), medial collateral ligament (MCL) or lateral collateral ligament (LCL), a knee brace can be used to both provide support and enhance extension strength, and thus reduce the load on the injured knee. Conventional knee braces that provide active assistance to knee extension are designed to yield when the knee is flexed, loading a torsion spring or compression spring in the process. The spring is loaded when the user bends their leg, and when extending their leg the spring unloads applying a force that augments the extension action. This also helps to support the user and prevent collapse if the injured knee buckles.

However, conventional springs do not provide sufficient force to significantly enhance knee extension or resist buckling of the knee. Additionally, a brace for a limb can be designed to provide a specific force profile or 'force curve' over the range of motion of the user's limb, and it is important to maintain a consistent force curve over the thousands of cycles that such a brace is likely to be used, which can be difficult to achieve using conventional springs.

Different kinds of springs have different loading characteristics, including different force curves, elastic deformation limits and plastic deformation limits. Certain applications have strict loading requirements over the operative range of the spring, and accordingly require a spring with fairly precise tolerances under light and heavy loads.

It would accordingly be advantageous to provide a mechanical substitute for a steel spring that is light-weight, has a consistent force curve over many thousands of cycles, and provides effective enhancement of the knee extension action in cases where strength enhancement is needed and resistance to buckling of the knee.

Hydraulic compression springs, commonly known as "liquid die springs", are known for use in the tool and die industry. In a liquid die spring a piston compresses a liquid to load the spring, and the potential energy of the spring is released when the compressive force is removed from the piston.

Liquid die springs have a very low compression ratio and a smooth force curve, making them well suited for short-stroke, highly linear applications such as tool and die machinery. However, a significantly longer stroke is required for applications such as knee braces, and this is problematic given the forces Forcing the piston into the spring can be equivalent to applying up to a 1500 lb. end load on a 0.125" steel rod that is more than an inch long. The piston will buckle unless it is very carefully guided, which can damage or destroy the piston, the seal, or both.

BRIEF DESCRIPTION OF THE DRAWINGS

In drawings which illustrate by way of example only a preferred embodiment of the invention, FIG. 1 is a perspective view of a first embodiment of a hydraulic tension spring compression element according to the invention.

FIG. 2 is a top plan view of the spring of FIG. 1.

FIG. 3 is a side elevation of the spring of FIG. 1.

FIG. 4 is a front elevation of the spring of FIG. 1, with the cylinder in the rest position.

FIG. 5 is a front elevation of the spring of FIG. 1, with the cylinder in the loaded position.

FIG. 6 is a front cross-sectional elevation of the spring of FIG. 1 taken along the line 6-6 in FIG. 2.

FIG. 7 is a front cross-sectional elevation of the spring of FIG. 6 taken along the line 7-7.

FIG. 8 is a front cross-sectional elevation of the spring of FIG. 6 taken along the line 8-8.

FIG. 20 is a side elevation of a further embodiment of a knee brace according to the invention in an extended position.

FIG. 21 is a side elevation of the embodiment of FIG. 25 in a flexed position.

DETAILED DESCRIPTION OF THE INVENTION

The invention will be described in the context of a knee brace 2 for humans. However, it will be appreciated that the principles of the invention apply equally to braces for other human body appendages and to braces for animals including (without limitation) horses, dogs and cats It will also be appreciated that a tension spring of the invention can advantageously be used in many other applications and the principles of the invention will apply equally. It will further be appreciated that all the advantages of the invention do not necessarily apply to every embodiment.

Figures 9A, 9B:
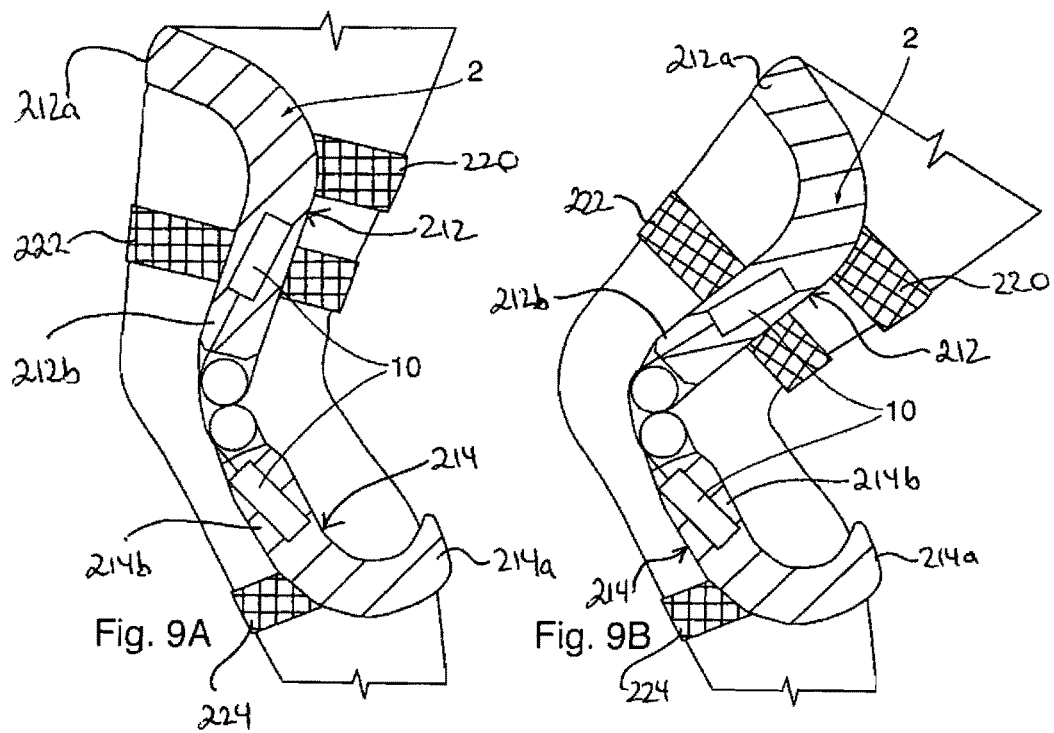
FIG. 9A is a schematic elevation showing the spring of FIG. 1 fixed to a knee brace in the rest position.
FIG. 9B is a schematic elevation showing the spring of FIG. 1 fixed to a knee brace in the loaded condition.

An embodiment of a compression element comprising a hydraulic tension spring 10 according to the invention is illustrated in FIGS. 1-5. The spring 10 comprises a block 12 comprising opposed guide legs 14 maintained in fixed spaced apart relation by a base 16. Opposed interior faces of the legs 14 each provide a cord guideway 14a for receiving a cord 50, as described below, and in the preferred embodiment comprise one or more guide channels 14b. The frame 12 is preferably molded from hardened steel, or another strong, rigid material that resists substantial flexing under the maximum forces ordinarily encountered in the environment in which the spring 10 is used, for example a knee brace 2 as shown in FIGS. 9A and 9B.

The spring 10 further comprises a moving cylinder 20 having an open end 22 and a closed end 24. The cylinder 20 is preferably molded from hardened steel or another strong, rigid material and has a wall thickness which resists substantial flexing under the maximum forces ordinarily encountered in the environment in which the spring 10 is used. The cylinder 20 is mounted in the frame 12, and constrained to axial movement along the guide legs 14, in the preferred embodiment by a series of ball bearings 18 nesting in the guide channels 14b and complementary guide channels 20a formed along the longitudinal sides of the cylinder 20, best seen in FIGS. 6 and 7. The guide channels 14b, 20a are accordingly semi-circular in cross-section in the embodiment illustrated, complementing the size and shape of the ball bearings 18 when the cylinder 20 is mounted in the frame 12, as best seen in FIG. 2. The cylinder 20 is thus able to move between a rest position, shown in FIG. 4A, and a loaded position, shown in FIG. 4B.

The cylinder 20 comprises a liquid-impermeable cavity 26 defining a liquid containment space that is filled with a hydraulic fluid, for example a silicone-based liquid or other suitable hydraulic fluid having the desired compressibility characteristics. The closed end 24 of the cylinder 20 is preferably formed integrally with the cavity wall 28. A bushing 30, for example composed of hardened steel or another suitably durable material, capable of being formed to high-precision tolerances and withstanding the high pressures (e.g. up to 6,000 lbs. of force), is preferably threadedly engaged within the other end 22 of the cylinder 20 and retains a hydraulic seal 31 formed form polyethylene, Teflon or another suitable material, seen in FIG. 8, seated within the cylinder 20, to contain the hydraulic fluid.

A piston 40 is disposed through the bushing 30 and seal 31 into the cavity, the piston rod 42 slidably extending through a central axial opening 30a through the bushing 30 and seal 31 (seen in FIG. 8). One end of the piston rod 42 provides a foot 42a bearing against the frame 12, for example embedded in a recess 16a in the base 16. The other end of the piston 40 provides a piston guide 44 which is liquid-permeable and closely fitted to the cavity wall 28, to maintain the piston 40 in precise axial alignment during each stroke. Thus, when the cylinder 20 is in the rest position shown in FIG. 4 the liquid is in a substantially uncompressed condition.

The spring 10 further comprises a flexible, inelastic cord 50 for applying a loading force to the spring 10. The cord 50 may for example be composed of a polyethylene fibre, for example Honeywell Spectra™ high-strength light-weight polyethylene fibre, which has a very high tensile strength and a very low elasticity. The cord 50 extends through the frame 12, for example through an opening 16b through the base 16, and has an anchored end 51 restrained against movement into the frame 12, for example via enlargement 52 which is too large to traverse the opening 16b. As will be evident from the operation of the invention, described below, while it is necessary to restrain the anchored end 52 of the cord 50 from being pulled into the frame 12 when the cord 50 is tensioned, specifically where the anchored end 52 is anchored is a matter of choice depending upon the environment in which the spring 10 is used. It is possible to fix the anchored end 51 to any suitable structure, including a movable structure or another spring 10, as long as the cord 50 can be tensioned at the desired point to load the spring 10.

The cord 50 in the embodiment shown is thus anchored against the base 16 via anchored portion 51 and extends through the opening 16b. The cord 50 continues through the cord guideway 14a axially along one side 18 of the cylinder 20 (on the left in the orientation shown in the drawings). A tensioning portion 54 is disposed around the closed end 24 of the cylinder 20 and runs down the other cord guideway 14a (on the right in the orientation shown in the drawings) along the side of the cylinder 20. A free portion 56 of the cord is movable into and out of the frame 12, for example extending through opening 16c in the base 16.

The cord 50 thus wraps around the cylinder as shown, such that the cylinder 20 is in the rest position when the cord 50 is not being tensioned. It will be appreciated that the cord 50 could enter and exit the frame 12 at intermediate positions along the legs 14, and does not need to wrap completely around the sides and closed end 24 of the cylinder, but the embodiment illustrated is advantageous for obtaining the maximum leverage against the compressive resistance of the spring 10 during loading.

In operation, the frame 12 is fixed to a stable structure, for example the upper portion of the hinged knee brace 2 shown in FIGS. 9A and 9B, and the free end 56 of the cord 50 is fixed to a structure that moves in relation to the fixed frame, for example fixed to the lower portion of the hinged knee brace 2, either directly or fixed to another spring 10 which is in turn fixed to the lower portion of the hinged knee brace 2 as shown in FIGS. 9A and 9B. As the free portion 56 of the cord 50 is tensioned, for example when a user flexes their knee, the cylinder 20 is forced toward the base 16 of the frame 12 as shown in FIG. 4B, in relative terms causing the piston rod 42 to move further into the cylinder 20. The displacement of hydraulic fluid caused by the greater volume of piston rod 42 intruding into the cylinder compressing the hydraulic fluid in the cylinder 20 and loads the spring 10. As the tension on the cord 50 is reduced, for example when a user extends their knee, the hydraulic fluid decompresses, moving the cylinder 20 toward the rest position and releasing the potential energy in the spring 10 into the cord 50, assisting the extension motion.

Conventional liquid die springs have no space constraints relative to stroke length, and as such can use much thicker cylinders in comparison with their force output. Because some of the environments in which tension springs of the invention can be advantageously used require that the spring 10 be compact, for example in a knee brace 2 where there is limited room for a spring and weight is a factor, in a spring 10 according to the invention the stroke length can approach the length of the cylinder 20 itself, which is nearly one-half of the total height of the frame 12 in the embodiments illustrated. This requires a very small cylinder, with attendant reduction in the wall thickness of the cylinder and therefore reduced resistance to buckling. In order to prevent buckling, the piston 40 is precision-guided by the piston guide 44 to remain oriented axially with a very high precision throughout the entire stroke length. It is also advantageous in a spring 10 according to the invention to utilize a very thin bushing 30 in order to reduce the overall length of the frame 12, since the bushing thickness is added to the required height of the cylinder assembly.

Figure 10:
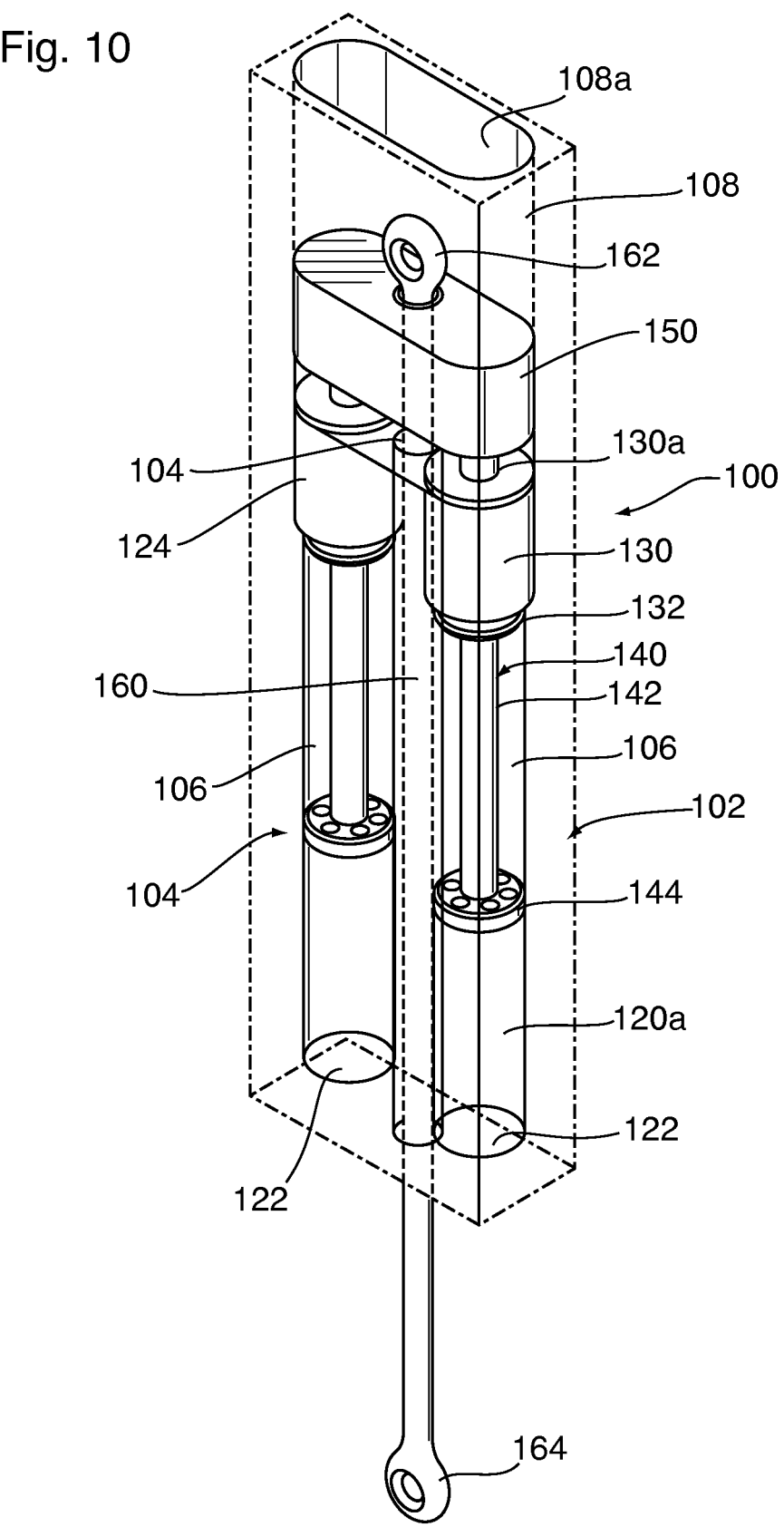
FIG. 10 is a perspective view of a further embodiment of a hydraulic tension spring according to the invention having multiple cylinders.

In further embodiments of the invention at least one piston moves relative to a stationary cylinder. For example, FIG. 10 illustrates a further embodiment of a hydraulic tension spring 100 according to the invention comprising multiple stationary cylinders with moving pistons. In this embodiment a pair of cylinders 120 are fixed within a block 102 and pistons 140 are movable to extend into and retract from the cylinders 120.

The block 102 thus comprises a cylinder portion 104 comprising a pair of cylinders 120 disposed longitudinally along the block 102 in parallel relation, in communication with a piston rod cap guide portion 108 containing a piston rod cap 150. The block 102 is preferably molded from hardened steel, or another strong, rigid material that resists substantial flexing under the maximum forces ordinarily encountered in the environment in which the spring 10 is used, for example a knee brace 2.

Figure 11A:
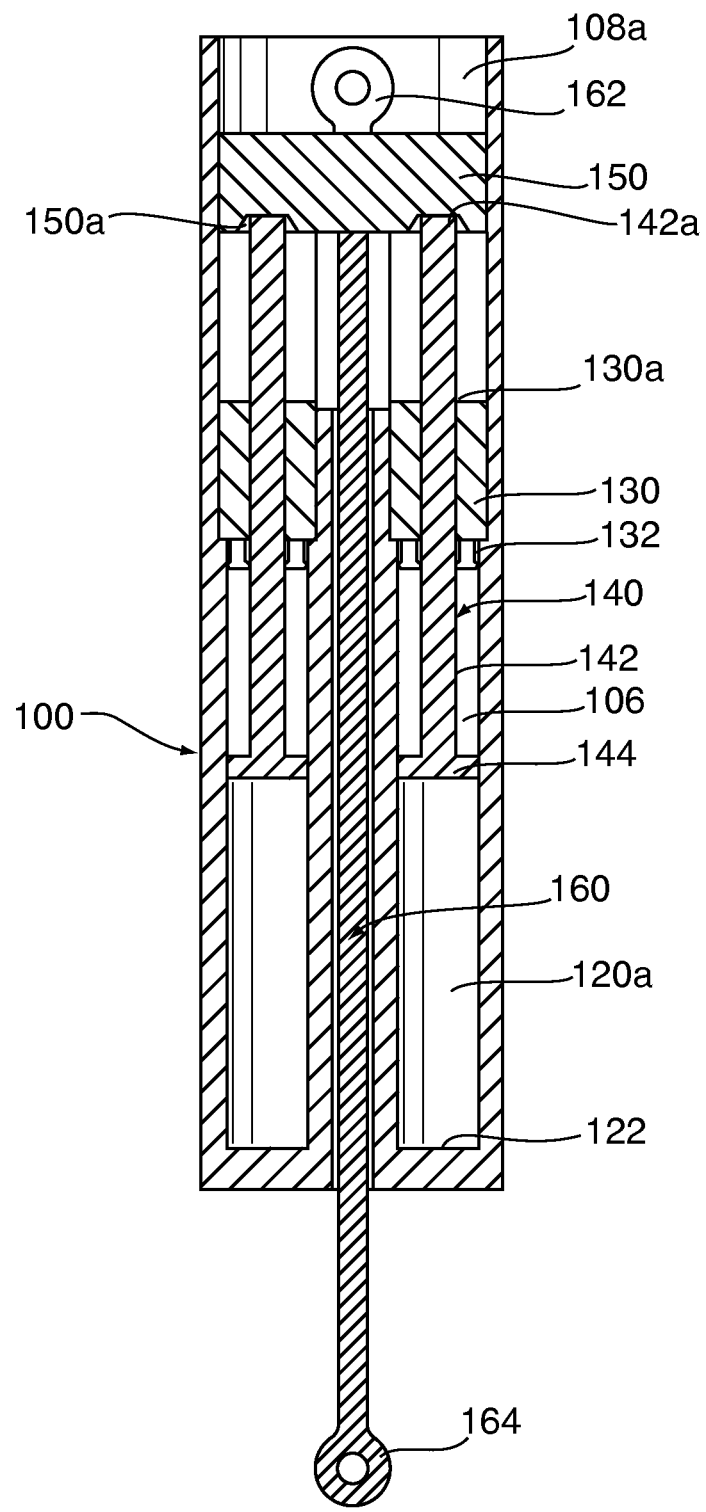
FIG. 11A is an elevational cross-section of the spring of FIG. 10 showing the spring in a rest condition.
Figure 11B:
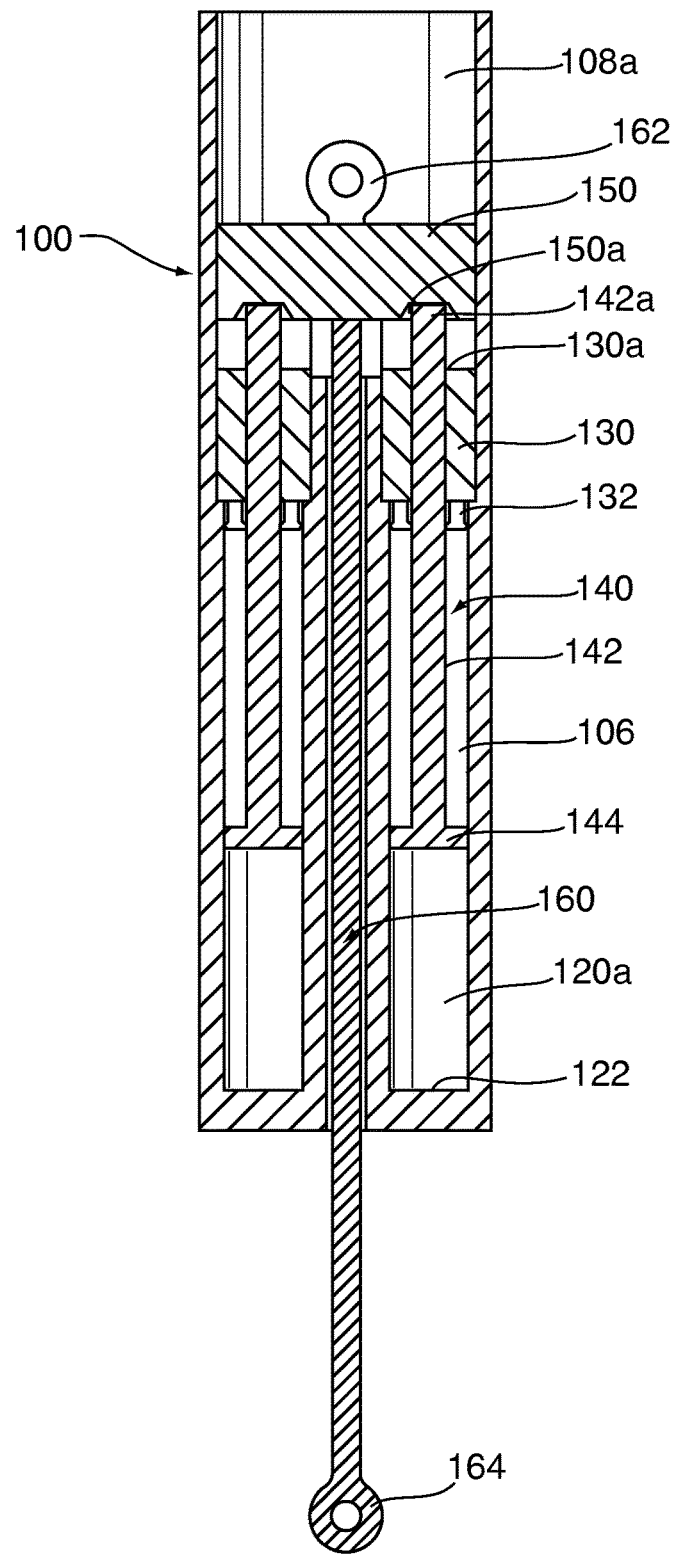
FIG. 11B is an elevational cross-section of the spring of FIG. 10 showing the spring in a tensioned condition.

Hydraulic fluid is compressible, but provides a very high resistance to compression. Accordingly, the pistons 140 preferably have a very small diameter, which means a very small volume in comparison to the volume of the cylinder 120. This allows for a full compression stroke of the piston 140, to the point shown in FIG. 11B, before the hydraulic fluid is compressed to the point that the user's weight cannot overcome the compressive resistance of the hydraulic spring 100.

The cylinders 120 each have a closed end 122 and an open end 124. Each cylinder 120 is defined by a liquid-impermeable wall having a thickness which resists deformation under the maximum forces ordinarily encountered in the environment in which the spring 10 is used. The closed end 122 of each cylinder 120 is preferably formed as an integral part of the block 102.

In this embodiment a piston 140 comprises a piston rod 142 slidably disposed through a seal retainer cap 130, for example composed of hardened steel or another suitably durable material capable of being formed to high-precision tolerances, disposed in the open end 124 of each cylinder 120. The seal retainer cap 130 may for example have a threaded exterior engaged to interior threading about the end of the cylinder 120. The piston rod 142 slidably extends from the cap guide portion 108 of the block 102 into the cylinder 120 through a central axial opening 130*a* through the seal retainer cap 130 and through hydraulic seal 132. The hydraulic seal 132 defines a liquid containment space 120*a* within the cylinder 120 that is filled with a liquid, for example a silicone-based liquid or other suitable hydraulic fluid having the desired compressibility characteristics. Thus, when the piston 140 is in the rest position shown in FIG. 11A the liquid entirely fills the liquid containment space 120*a*, and is in a substantially uncompressed condition.

In this embodiment the end of the piston rod 142 within the cylinder 120 is provided with a piston guide 144, which is liquid-permeable and thus moves freely through the liquid containment space 120*a* while retaining the piston rod 132 in precise axial alignment within the block 102. The opposite end of each piston rod 142 provides a foot 142*a* (seen in FIGS. 11A and 11B) against which the piston rod cap 150 bears, for example by lodging the ends of each piston rod 142 in a recess 150*a* to maintain the piston rods in position symmetrically about the centre of the piston rod cap 150 so that substantially equal force is applied to each piston rod 142. The piston rod cap 150 is constrained to axial movement relative to the cylinders 120 by the wall 108*a* of the cap guide portion 108 of the block 102.

A tensioning member, for example a tensioning rod 160, extends through a bore 152 disposed axially through the piston rod cap 150 at a position between the two piston rods 142, and extends through a bore 104 disposed axially between the two cylinders 120. An enlarged terminus 162 of the tensioning rod 160 prevents the tensioning rod 160 from slipping out of the bore 152 in the piston rod cap 150, essentially affixing the tensioning rod 160 to the piston rod cap 150, and the other end of the tensioning rod is accessible from outside the block 102 and preferably provides a connector, for example a loop 164, for affixing a cord or other flexible or rigid inelastic tensioning element (not shown).

In the operation of this embodiment, the block 102 is fixed in position, for example affixed to the cuff of a knee brace, and a tensioning element (not shown) is affixed to the connector 154 with the spring 100 in the rest position shown in FIG. 10A. As tension is applied to the tensioning element and transmitted to the tensioning rod 160, the enlargement 162 draws the piston rod cap 150 toward the cylinders 140. The piston rod cap 150 in turn forces the pistons 140 into the cylinders 120, to the tensioned position shown in FIG. 10B. The increasing volume of piston rod 142 within the liquid containment space 120*a* as the piston rod 142 enters the cylinder 108 displaces the hydraulic fluid, compressing the hydraulic fluid in the liquid containment space 120*a* and loading the spring 100. When the tension is released from the tensioning rod 160, the spring 100 releases, forcing the piston 140 to return to the rest position of FIG. 10A and in the process imparting the stored potential energy to the load.

It will be appreciated that in the multiple-cylinder embodiment, additional cylinders 120 may be provided as long as all cylinders 120 are distributed symmetrically about an axis containing the tensioning rod 160. In this fashion tension applied to the tensioning rod 160 is distributed equally amongst the cylinders, ensuring that the tensioning force is applied axially to each piston 140 so as to avoid buckling.

It will also be appreciated that the piston guide 144 is preferably shaped to be complementary to the cross-section of the cylinder 120, for example circular in the embodiment illustrated, for maximum lateral stability. However, the piston guide 144 need only contact the wall of the cylinder 120 at a sufficient number of points to maintain the axial orientation of the piston 140, as shown centred within the cylinder 120, for example at three points spaced circumferentially equally about the cylinder 120.

Figure 12:
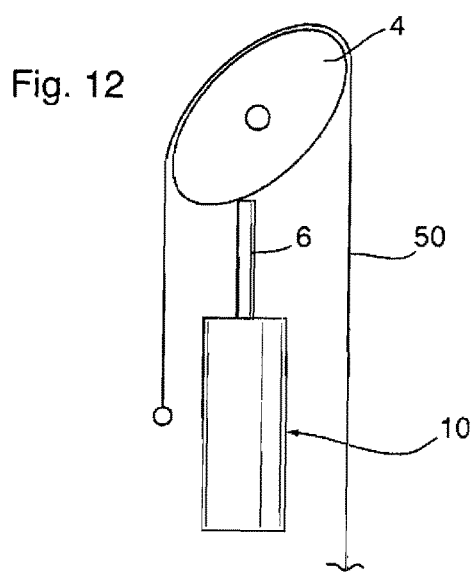
FIG. 12 is a schematic elevation showing an alternate tensioning mechanism for the spring 10, interposing an eccentric element 4 to provide a non-linear force curve.

FIG. 12 illustrates an embodiment in which the spring 10 is mounted adjacent to an eccentric element, for example cam 4 which is rotatably mounted to the structure to which the spring 10 is fixed (e.g. a knee brace 2). As tension is applied to the cord 50, the cam 4 rotates, applying a force to the plunger 6 which increases as the cam is rotated. The plunger 6 ion turn transfers this force to the spring (e.g. bearing against the outer face 24 of the cylinder 20 shown in FIGS. 1-8).

An embodiment of a knee brace 210 for augmenting extension of a user's knee 6 is illustrated in FIGS. 9A and 9B by way of example. The knee brace 210 conventionally comprises an upper arm 212 having an engaging portion 212a for engaging against the femoral portion 2 of a user's leg, for example the front of the femoral portion 2 as illustrated, and an attachment portion 212b; and a lower arm 214 having an engaging portion 214a for engaging against the tibial portion 4 of the user's leg, for example the rear of the tibial portion 4 as illustrated, and an attachment portion 214b. The upper arm 212 is formed with a contour that comfortably engages against the user's quadricep 2, which may be padded for additional comfort, and may be secured to the leg by a top strap 220 and an upper cruciate strap 222 as is conventional. The lower arm 212 is formed with a contour that comfortably engages against the user's calf 4, which similarly may be padded for additional comfort, and may be secured to the leg by a bottom strap 224 and optionally a lower cruciate strap (not shown).

The lower arm attachment portion 214b is pivotally connected to the upper arm attachment portion 212b as at pivots 216, 217. Each pivot 216, 217 is rotationally affixed to a connecting element such as a gusset 218 (best seen in FIG. 17) so that the upper and lower arms 212, 214 can pivot relative to the gusset 218, and thus relative to each other. As shown in FIGS. 9A and 9B, when the knee brace is in position the pivots 216, 217 are disposed on either side of the leg along the axis of rotation of the knee 6, and the arms 212, 214 freely pivot relative to one another as the knee 6 flexes and extends. In use the brace 210 is positioned so that the two pivots 216, 217 are aligned with the two pivot points in the knee 6. In other embodiments the arms 212, 214 may be geared to each other, or otherwise coupled by a linkage such that they rotate together. The knee brace 210 illustrated applies a force to assist the user in extending the knee 6 when the knee 6 has been flexed, the force being supplied by a tension spring according to the invention fixed to each of the upper and lower arms 212, 214.

Figure 13:
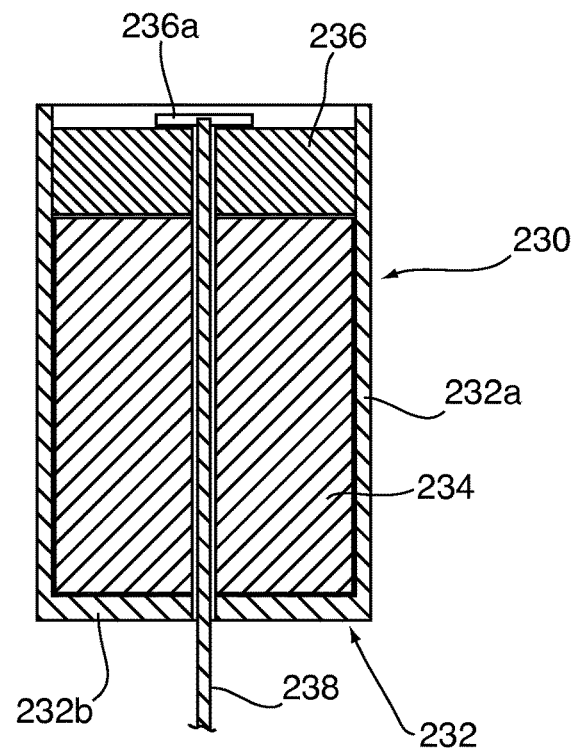
FIG. 13 is a side elevation of a further embodiment of a compression element utilizing a compressible elastomer, shown in the relaxed condition when the knee is extended.
Figure 14:
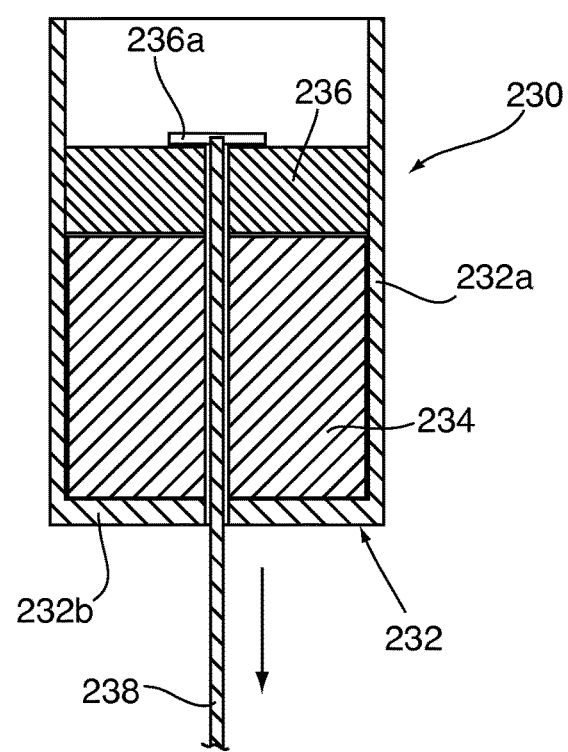
FIG. 14 is a side elevation of the compression element of FIG. 13 in the loaded condition when the knee is flexed.
Figure 15:
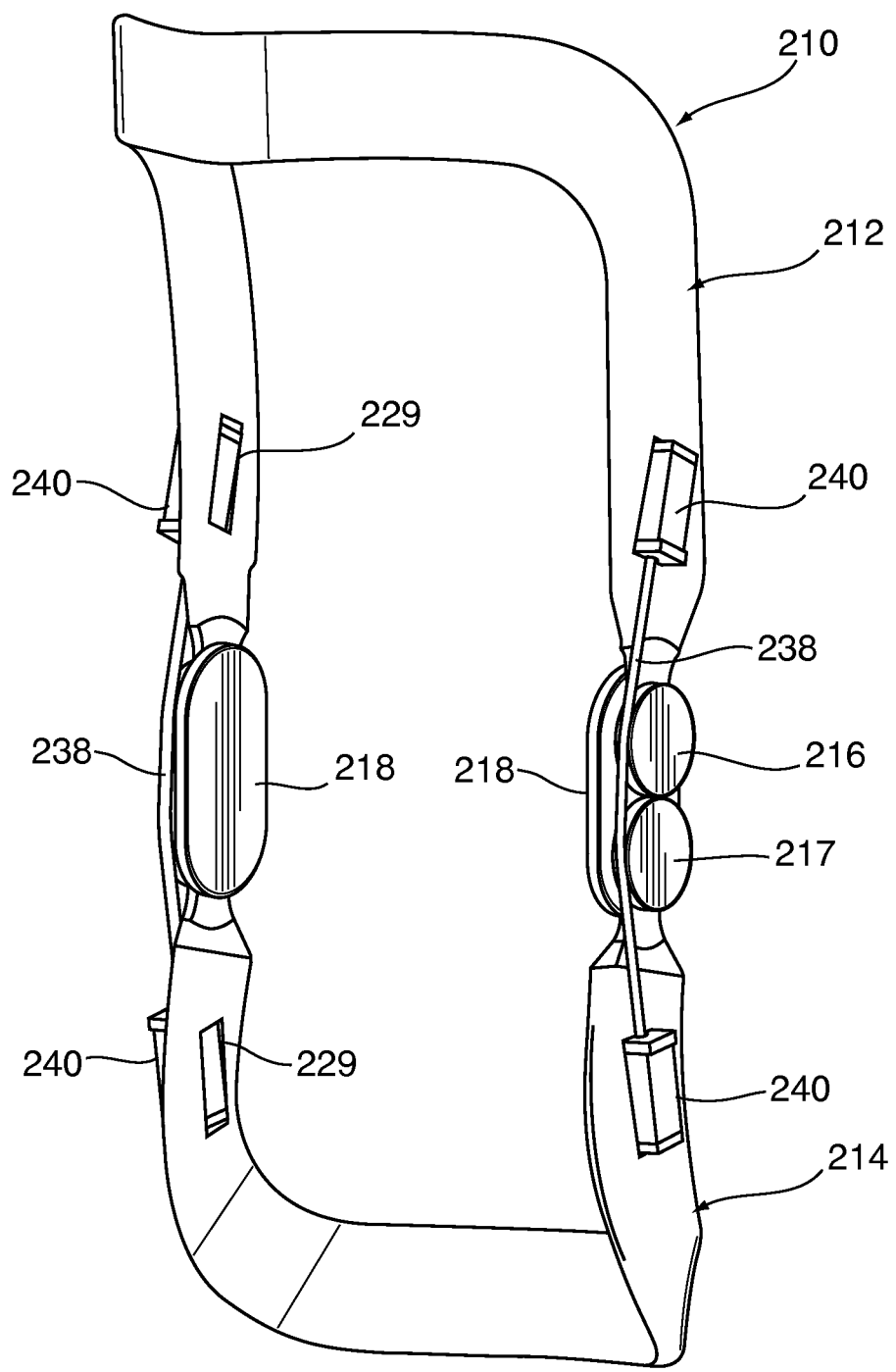
FIG. 15 is a front perspective view of an embodiment of a knee brace utilizing the compression element of FIG. 13.
Figure 16:
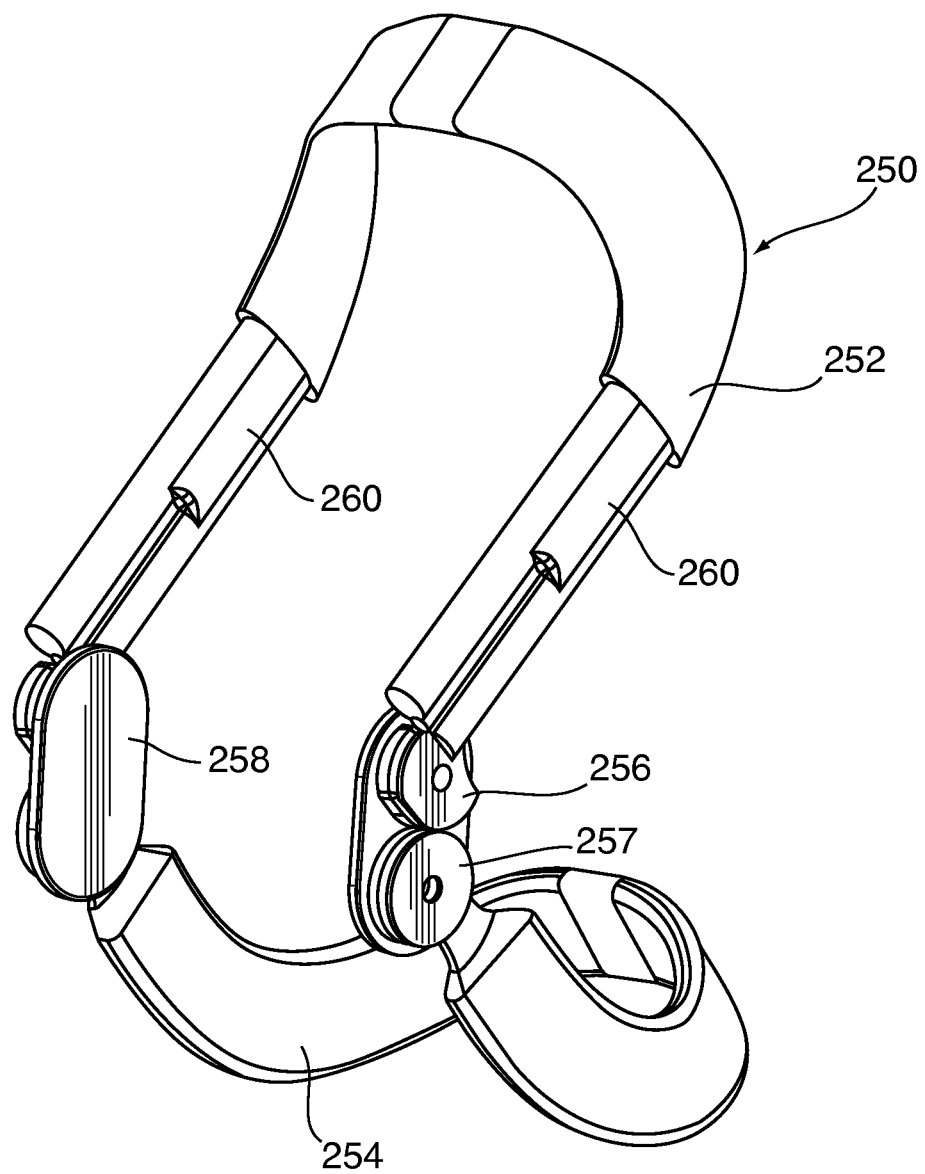
FIG. 16 is a perspective view of an embodiment of a knee brace according to the invention utilizing a liquid die spring compression element.

A further embodiment of a tension spring according to the invention comprises a compression element 230, illustrated in FIGS. 13 and 14. The compression element 230 comprises a rigid base 232, in the embodiment shown in FIGS. 15 and 16 a hollow cylinder having a floor 232a and a wall 232b. The compression element 230 may be formed integrally with the arm 212, 214 as shown, or may be a separate component which is bolted, riveted or otherwise fastened to the exterior surface of the arm 212 or 214. FIG. 15 for example illustrates an embodiment of the knee brace 210 utilizing compression members 240 having a generally rectangular cross-section, fixed within openings 229 in the upper and lower arms 212, 214.

In this embodiment the compression element 230 comprises an elastomeric element 234 seated against the floor 232a of the base 232, and a rigid head 236 spaced from the floor 232a of the base 232 and overlaying the elastomer 234. The base 232 and head 236 may for example be composed of metal or a rigid plastic strong enough to withstand the force of the elastomer 234 when under compression, as described below. The elastomer 234 may for example be a block of polyurethane, preferably having a hardness in the range of 25 to 70 Shore D, most preferably in the range of 30 to 60 Shore D, and thus being compressible to a desired extent depending upon the degree of extension augmentation required for a particular application or individual.

The elastomer 234 is essentially sandwiched between the floor 232a of the base 232 and the head 236. It is possible to form the base 232 as a floor only, without the wall 232b, which would still allow for the compressive loading of the compression element 230 in the manner described below. However, providing a rigid wall 232b to contain the elastomer 234 advantageously increases the compression resistance of the elastomer 234, because the wall 233b prevents the elastomer 234 from expanding laterally as the head 236 is drawn toward the base 232 in the manner described below. Also, forming the base 232 as a container is beneficial aesthetically and keeps the elastomer clean. Further reduction of the compressibility of the elastomer 234 may be achieved by intermixing elastomeric elements with incompressible elements such as metal washers, for example by separating the elastomer block into pieces and interspersing metal washers between the elastomer pieces.

In this embodiment a flexible tensioning element such as a substantially inelastic cord 238 is fixed to the head 236 through the elastomer 234 and the base 232, as best seen in FIGS. 13 and 14. Applying tensile force to the cord 238 draws the head 236 toward the base 232 to compress the elastomer 234. The cord 238 may be retained through the head 236 by a washer 236a crimped or clinched to grasp the end of the cord 238. Alternatively, the head 236 may be formed around the cord 238, or any other suitable manner of engagement of the cord 238 to the head may be used.

The other end of the cord 238 is attached to the other arm 212 or 214. In the preferred embodiment, a compression element 230 is fixed to both of the upper and lower arms 212, 214, which reduces the force required to achieve the same amount of compression when the knee is flexed, in comparison to using a single compression element 230.

Figure 17:
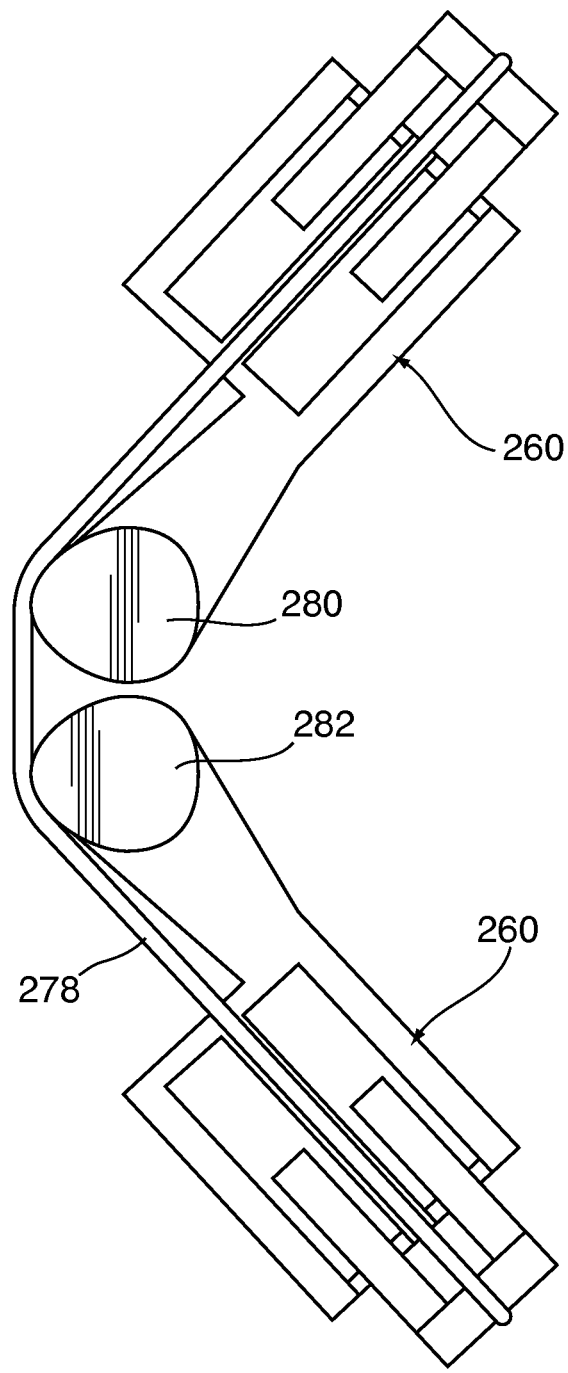
FIG. 17 is a schematic perspective view of an embodiment of the tensioning system having an ovate pivot.

The cord 238 is fixed between the two compression elements 230 such that it runs over a tensioning member, and is taut when the compression elements 230 are in the fully unloaded condition shown in FIG. 15. In the embodiment shown pivots 216 and 217 form the tensioning member. The cord 238 may be retained about the pivots 216, 217 in any conventional fashion, for example the pivots 216, 217 may provide a circumferential slot through which the cord 238 runs as shown in FIG. 17, or the cord 238 may be retained about the pivots 216, 218 by a housing or cap (not shown) which forms a channel preventing the cord 238 from slipping off of the pivots 216, 217 as tension is applied to the cord 238. Alternatively, a separate tensioning member such as a post or rivet (not shown) may be provided to retain an intermediate portion of the cord 238 near the front of the brace 210 around the region of the knee 6.

Figure 23:
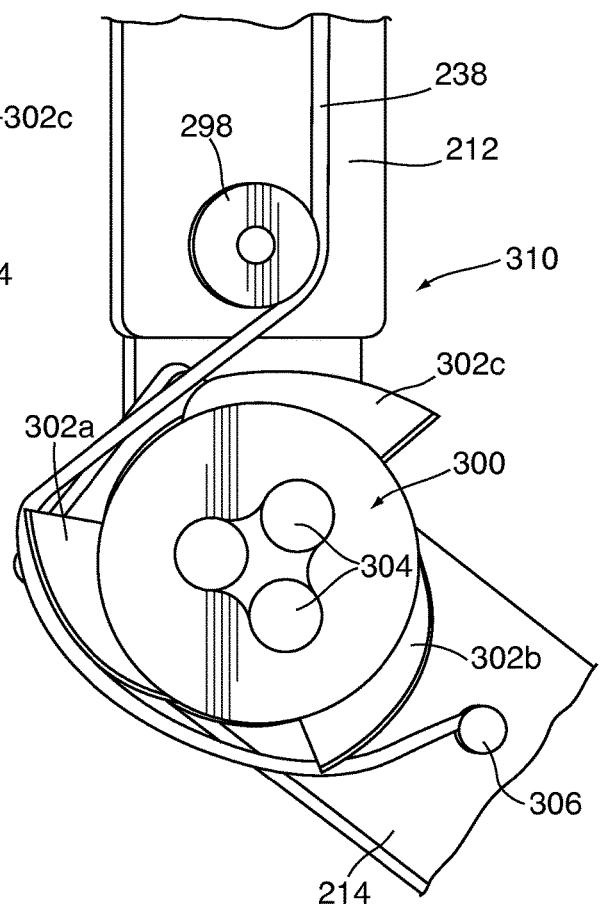
FIG. 23 is a side elevation of the embodiment of FIG. 26 in the flexed position.

The cord 238 is preferably composed of a polyethylene fibre, for example Honeywell Spectra™ high-strength lightweight polyethylene fibre, which has a very high tensile strength. This type of material also has a very low coefficient of friction, so it easily slides along the pivots 216, 217 without significant wear or resistance to the user's motion. Alternatively, the tensioning member may comprise rollers (not shown), if desired, to reduce friction. The pivots 216, 217 can be free-rotating, fixed to the gusset 218, or fixed to either or both of the arms 212, 214 (and thus rotating with the arms 212, 214); and/or one or more separate wheels 256, 257 may be fixed to or near either or both of the pivots 216, 217 to form a tensioning member or tensioning members, for example as shown in FIG. 23. There may be one or two pivots 216, 217. In embodiments where there are two cylinders 230, a single cord 238 could be attached to both cylinders 230 or two cords 238 could be affixed to or near the gusset. In embodiments where there is one cylinder 230, the free end of the cord 238 can be attached to the gusset, the second pivot 216 or 217, or the other arm 212 or 214.

In use, the user affixes the knee brace 210 to their leg via straps 220, 222 and 224 in conventional fashion. With the brace 210 in the extended position shown in FIG. 15, the compression elements 230 are in a relaxed condition with no compressive load on the elastomer block 234. When the user flexes their knee 6 a force is applied to the tensioning cord 238 as the compression elements 230 are forced away from the tensioning member (pivots 216, 217). This tensions the cord 238, which draws on the head 236 of each compression element and compresses the elastomeric block 234, as shown in FIG. 14, loading the compression elements 230, the compressive load increasing as the knee 6 is flexed. Upon removal of the flexing force the compression elements 230 release the stored energy and apply a restoring force to urge the knee brace 210 back to the extended position, augmenting the user's extension force.

Providing a compression element 230 on each of the upper and lower arms 212, 214 allows the compression elements 230 to be smaller (and therefore lighter), while still providing the required length of travel and recovery force needed to allow the user to fully flex and extend the knee. In the embodiment illustrated in FIG. 16, the compression element comprises a hydraulic spring, for example the spring 100 illustrated in FIG. 10. As in the hydraulic spring 10 of FIGS. 1 to 8, the hydraulic spring 100 relies on fluid compression to load the spring, and thus in this embodiment a single compression element can provide sufficient restoring force to assist with knee extension.

The above embodiments provide relatively uniform linearly increasing compression and release curves, so that the same amount of strength is required to load the compression element 230 or 260 whether at the beginning or the end of the path of travel of the knee brace; and likewise the same amount of assistive force is provided by the compression element 230 or 260 whether at the beginning or the end of the path of travel of the knee brace.

Figures 18, 19:
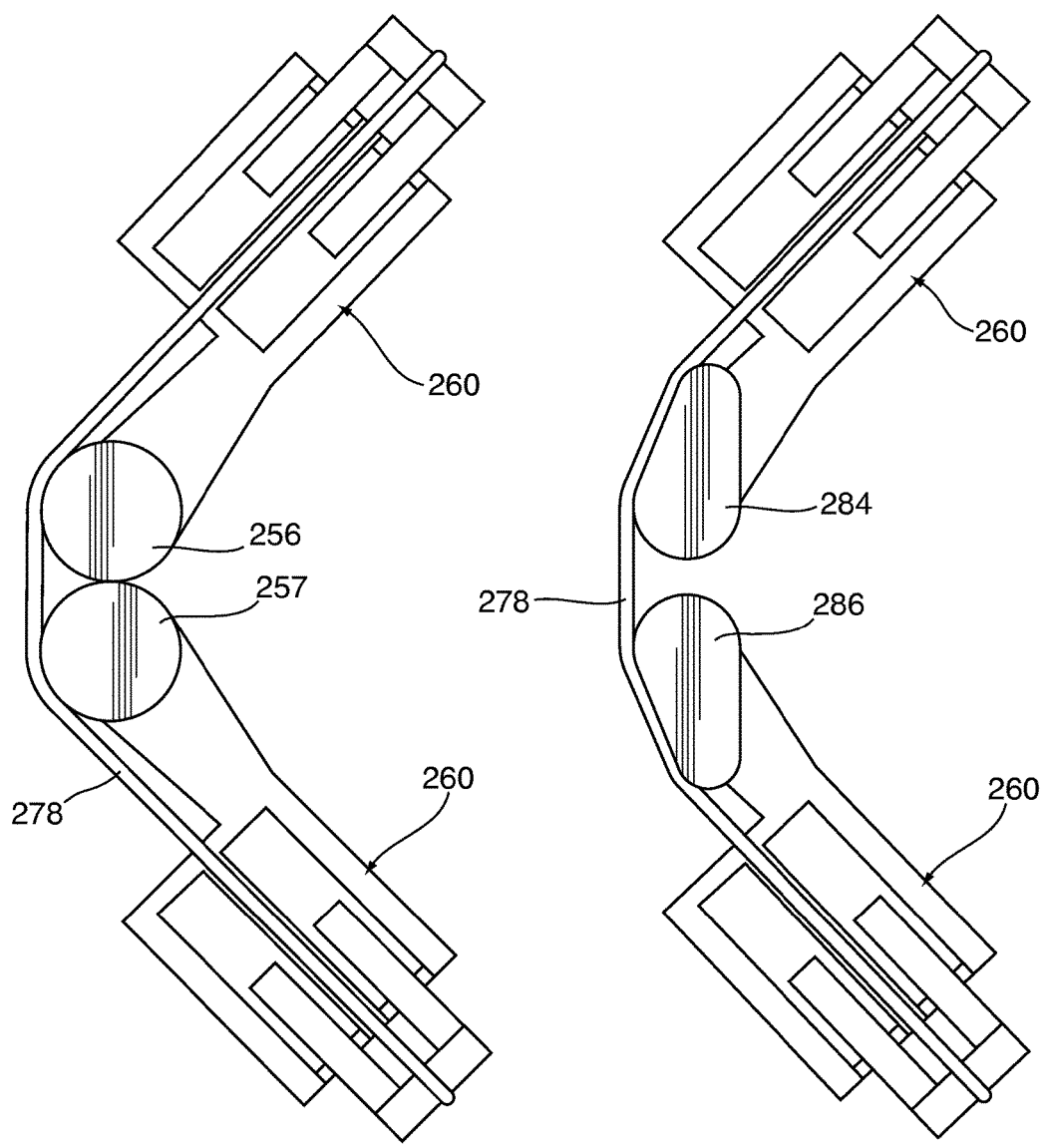
FIG. 18 is a schematic perspective view of an embodiment of the tensioning system having a circular pivot mounted eccentrically.
FIG. 19 is a schematic perspective view of an embodiment of the tensioning system having an elongated pivot.

In all embodiments it is possible to change the load characteristics at different points along the path of travel of the knee brace, for example by mounting circular pivots 256, 257 (or 216, 217) eccentrically, or by using oblong or otherwise non-circular pivots 280, 282 or 284, 286, as shown respectively in FIGS. 17 and 19. In these embodiments, because the pivot rotates with the arm, the length of cord 278 which is drawn out of the compression element 260 over a given length of travel of the lower arm 254 relative to the upper arm 252 varies, depending upon the shape and position of the pivot at any specific point in the path of travel. Thus, in cases where a particular pathology may require a greater restoring force or lesser loading force at one or more specific points in the flexing cycle, the pivot can be designed to provide a non-linear force curve to accentuate assistance or reduce the force required for loading at the specific point or points.

FIGS. 20 and 21 illustrate an embodiment of the invention having a single compression element 260 disposed on the upper arm 212. The cord 278 in this embodiment extends over pivot 292 affixing the upper arm 212 to the gusset 218, retained against dislodgement by a retaining wheel 294 which may be fixed or free-rolling. A further pivot 290 affixing the lower arm 214 to the gusset 218 is ovate and oriented such that the resistance of the compression element 260 to flexing of the brace 10 increases as the angle between the arms 212, 214 diminishes.

Figure 22:
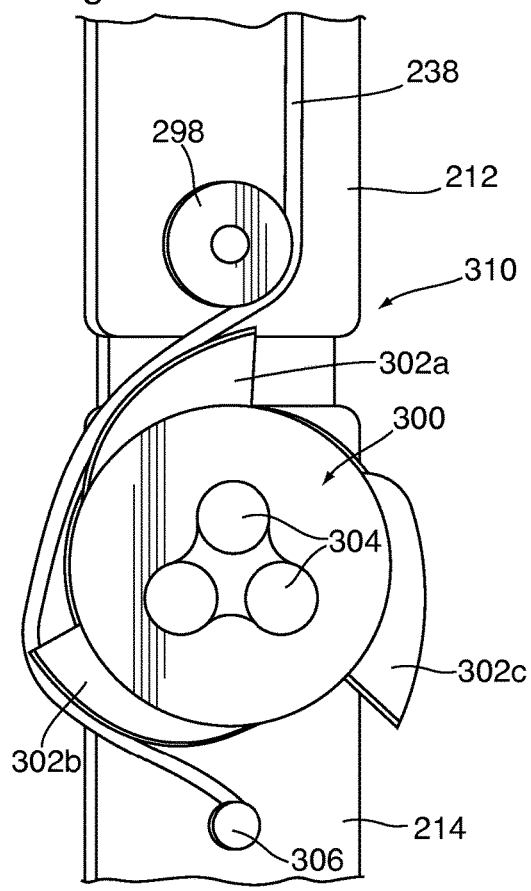
FIG. 22 is a partial side elevation of a further embodiment of the invention having cams projecting from the tensioning member.

A further embodiment of the invention is illustrated in FIGS. 22 and 23. In this embodiment the brace 310 provides tensioning members comprising a free-rolling wheel 298 cooperating with a rotationally fixed wheel 300, which for example is affixed to the lower arm 214 by pins 304. Cams 302a, 302b and 302c projecting from wheel 300 each provide an irregular surface that engages the cord 238. Similar to the previous embodiments, as the brace 310 is pivoted to the flexed position shown in FIG. 23 tension is imparted to the cord 238 by the increased displacement between the wheel 298 and the anchoring point 306 on the lower arm 214. However, this embodiment also provides a differential increase in tension, because as cam 302a turns in the direction of the cord 238 when the brace 310 is flexed, the cam 302a also pushes the cord 238 further away from the centre of the wheel 300.

In the embodiment shown in FIGS. 22 and 23, cams 302a, 302b and 302c have different profiles. Thus, each cam 302a, 302b, 302c provides a different degree of differentially increasing tension as the brace 310 is flexed. In the preferred embodiment the wheel 300 can be detached from the lower arm 214 and re-attached in a different orientation, so that a different one of the cams 302a, 302b and 302c engages the cord 238 when the brace 310 is flexed. The wheel 300 is illustrated with three cams 302a, 302b and 302c evenly spaced about the wheel 300, and thus is adapted to be mounted to the lower arm 214 in any one of three positions via pins 304. However, if desired more cams can be provided for greater versatility.

Various embodiments of the present invention having been thus described in detail by way of example, it will be apparent to those skilled in the art that variations and modifications may be made without departing from the invention. The invention includes all such variations and modifications as fall within the scope of the appended claims.

I claim:

1. A brace for augmenting extension of a user's limb about a joint, comprising
   an upper arm having an engaging portion for engaging against the user's limb above the joint, and an attachment portion,
   a lower arm having an engaging portion for engaging against the user's limb below the joint, and an attachment portion, the lower arm being pivotable relative to the upper arm,
   at least one compression element disposed in fixed relation to at least one of the upper and lower arms, and
   a substantially inelastic tensioning element affixed to the other of the upper and lower arms over at least one tensioning element tensioning member such that applying a force to bend the brace to a flexed position loads the compression element, and upon removal of the flexing force the compression element applies a restoring force to urge the brace back to an extended position, the compression element comprising a hydraulic tension spring disposed in fixed relation to at least the other of the upper and lower arms, comprising a pair of cylinders mounted within a frame, each cylinder having a sealed portion defining a liquid containment space, for each of the pair of cylinders, a piston comprising a piston rod, the piston rod comprising a compressing portion having a smaller diameter than the cylinder and extending axially through a hydraulic seal into the liquid containment space, and an external portion accessible from outside the liquid containment space, one of the cylinder and the piston being fixed relative to the frame and the other of the cylinder and the piston being movable axially relative to the frame, a guide for maintaining the movable one of the cylinder and the piston oriented axially relative to the frame, and a compression element tensioning member bearing against the movable one of the at least one cylinder and the piston, for compressing the at least one cylinder relative to the piston, whereby when the frame is fixed in place and tension is applied to the tensioning element tensioning member, the compressing portions of the piston rods intrude further into the liquid containment space, compressing the hydraulic fluid and loading the spring.

2. The brace of claim 1 wherein the tensioning element is attached to the other of the upper and lower arms via a second compression element fixed to the other of the upper and lower arms.

3. The brace of claim 2 wherein the lower arm attachment portion and the upper arm attachment portion are pivotally connected to a connecting element.

4. The brace of claim 3 wherein the at least one tensioning element tensioning member comprises at least one pivot connecting the upper arm or the lower arm to the connecting element.

5. The brace of claim 4 wherein the at least one pivot comprises a circumferential groove for retaining the tensioning element.

6. The brace of claim 1 comprising a plurality of tensioning element tensioning members.

7. The brace of claim 1 wherein the at least one tensioning element tensioning member is mounted eccentrically.

8. The brace of claim 1 wherein the at least one tensioning element tensioning member is non-circular.

9. The brace of claim 1 wherein the at least one tensioning element tensioning member is free-rotating.

10. The brace of claim 1 wherein the at least one tensioning element tensioning member is fixed in relation to one of the upper and lower arms or a gusset joining the arms together.

11. A brace for augmenting extension of a user's limb about a joint, comprising an upper arm having an engaging portion for engaging against the user's limb above the joint, and an attachment portion, a lower arm having an engaging portion for engaging against the user's limb below the joint, and an attachment portion, the lower arm being pivotable relative to the upper arm, a substantially inelastic tensioning element affixed to one of the upper and lower arms over at least one tensioning element tensioning member such that applying a force to bend the brace to a flexed position loads a compression element, and upon removal of the flexing force the compression element applies a restoring force to urge the brace back to an extended position, and the compression element comprising at least one hydraulic tension spring disposed in fixed relation to at least the other of the upper and lower arms, comprising at least one cylinder having a sealed portion defining a liquid containment space, for each of the at least one cylinders, a piston comprising a piston rod, the piston rod comprising a compressing portion having a smaller diameter than the cylinder and extending axially through a hydraulic seal into the liquid containment space, and an external portion accessible from outside the liquid containment space, one of the cylinder and the piston being fixed relative to a frame and the other of the cylinder and the piston being movable axially relative to the frame, a guide for maintaining the movable one of the cylinder and the piston oriented axially relative to the frame, and a compression element tensioning member bearing against the movable one of the at least one cylinder and the piston, for compressing the at least one cylinder relative to the piston, whereby when the frame is fixed in place and tension is applied to the compression element tensioning member, the compressing portion of the piston rod intrudes further into the liquid containment space, compressing the hydraulic fluid and loading the spring.

12. The brace of claim 11 wherein applying a tensioning force to the compression element tensioning member draws a piston rod cap against the piston, the piston rod cap being positioned so as to apply force axially to the external portion of the piston rod.

13. The brace of claim 11 wherein the hydraulic tension spring comprises a plurality of cylinders and pistons, wherein the piston rod cap is positioned so as to apply force axially to the external portions of each of the piston rods and the compression element tensioning member applies force to the piston rods centrally between the cylinders so as to apply the axial force equally to the external portion of each piston rod.

14. The brace of claim 11 wherein the tensioning element is attached to the one of the upper and lower arms via a second compression element fixed to the one of the upper and lower arms.

15. The brace of claim 14 wherein the lower arm attachment portion and the upper arm attachment portion are pivotally connected to a connecting element.

16. The brace of claim 15 wherein the at least one tensioning element tensioning member comprises at least one pivot connecting the upper arm or the lower arm to the connecting element.

17. The brace of claim 16 wherein the at least one pivot comprises a circumferential groove for retaining the tensioning element.

18. The brace of claim 11 wherein the at least one tensioning element tensioning member is mounted eccentrically.

19. The brace of claim 11 wherein the at least one tensioning element tensioning member is non-circular.

20. The brace of claim 11 wherein the at least one tensioning element tensioning member is free-rotating.

* * * * *